United States Patent [19]
Fujita et al.

[11] Patent Number: 5,948,752
[45] Date of Patent: Sep. 7, 1999

[54] SUPPRESSORY AGENTS AGAINST HYPERCOAGULATION

[75] Inventors: Mitsugu Fujita, Inami-cho; Yoshikazu Komurasaki, Miki; Keihide Koh; Hiromichi Ishikawa, both of Kobe, all of Japan

[73] Assignee: JCR Pharmaceuticals Co., Ltd., Hyogo, Japan

[21] Appl. No.: 09/132,534

[22] Filed: Aug. 11, 1998

[30] Foreign Application Priority Data

Aug. 11, 1997 [JP] Japan .................................. 9-230294

[51] Int. Cl.⁶ ...................................... A61K 38/57
[52] U.S. Cl. ..................................... 514/8; 514/21
[58] Field of Search ................... 530/350, 395, 530/380, 381; 514/8, 12, 21

[56] References Cited

FOREIGN PATENT DOCUMENTS 0 280 135  8/1988  European Pat. Off. .
93/00926  1/1993  WIPO .

OTHER PUBLICATIONS

Suzuki, Protein C Inhibitor Methods In Enzymology, vol. 222, pp. 385–399, 1993.

Marlar et al., "Serial studies of protein C and its plasma inhibitor in patients with disseminated intravascular coagulation", *Blood*, vol. 66, No. 1, 1985, pp. 59–63.

Ecke et al., "Inhibition of the tissue kallikrein by protein C inhibitor", *The Journal of Biological Chemistry*, vol. 267, No. 10, 1992, pp. 7048–7052.

Rezaie, et al., "Protein C inhibitor is a potent inhibitor of the thrombin–thrombomodulin complex", *The Journal of Biological Chemistry*, vol. 270, No. 43, pp. 25336–25339 (1995).

*Primary Examiner*—Jeffrey E. Russel
*Attorney, Agent, or Firm*—Jacobson, Price, Holman & Stern, PLLC

[57] ABSTRACT

According to the present invention, there are provided suppressory agents against hypercoagulation which comprise as an effective ingredient protein C inhibitor with a molecular weight of 54 to 57 kDa (DS-PAGE) being capable of suppressing function of the blood coagulation system.

3 Claims, 2 Drawing Sheets

|  | M | 1 | 2 |
|---|---|---|---|
| kDa | | | |
| 200→ | | | |
| 116→ | . . | | |
| 66.3→ | ( l | | |
| 42.4→ | l l | ▬ | ▬ |
| 30.0→ | — | | |
| 17.2→ | — | | |

FIG. 1

SUPPRESSORY AGENTS AGAINST HYPERCOAGULATION

The present invention relates to suppressory agents against hypercoagulation which comprise as an effective ingredient protein C inhibitor with a molecular weight of 54 to 57 kDa being capable of suppressing function of the blood coagulation system, as obtained through purification and separation from human urine or blood.

BACKGROUND OF THE INVENTION

Referring to the diseases caused by hypercoagulation, disseminated intravascular coagulation (hereinafter referred to briefly as "DIC") is representative. DIC is a disease in which tissue factor exposed through cytoclasis by malignant tumors or bacterial infections (action of endotoxins produced by bacteria) gets into contact with blood to thereby cause hypercoagulation, or hyperfunction of the blood coagulation system (marked increases in blood thrombin level), with resultant formation of multiple thrombi in the systemic microvessels (the coagulation-dominant type DIC). Since the fibrinolytic system of DIC patients is normal, however, there is induced secondary fibrinolysis to dissolve the formed clots, resulting in repetition of blood coagulation-thrombolysis within the patient body at enhanced frequencies (i.e., the compensatory DIC). On the occasion of this, the blood levels of fibrin/fibrinogen degradation products (hereinafter referred to briefly as "FDP") are caused to rise. When the disease becomes severe, furthermore, consumption of blood coagulation factors (e.g., fibrinogen) exceeds their biosynthesis to create a serious bleeding tendency (i.e., the fibrinolysis-dominant type DIC), leading to occasional death.

DIC is a disease which, being accompanied with so marked an increase in blood thrombin levels as it may in some instances called thrombocythemia or thrombocytosis, is therefore characterized by hypercoagulation, and the major drugs heretofore employed for DIC treatment include heparin (a mixture of heparins with molecular weights ranging from 4,000 to 40,000), low-molecular-weight heparin (heparin with a molecular weight of 4,000 to 5,000 fractionated from heparin) and antithrombin III concentrated preparations.

Heparin currently used in the treatment of DIC exerts action not only on thrombin (the major factor of the blood coagulation system) but also blood coagulation factor Xa to thereby inhibit blood coagulation, wherein the compound acts mainly as a mediator in the reaction between thrombin and antithrombin III (a thrombin inhibitory factor present in blood); in other words, heparin inhibits indirectly blood coagulation. Heparin is repeatedly utilized many times within the living body in the said inhibition reaction, whereas antithrombin III, upon formation of a complex with thrombin, undergoes rapid metabolism and disappears. This creates a tendency for the DIC patients to become deficient in antithrombin III, with the consequent, occasional need to supplement with antithrombin III. In Japan, nevertheless, the antithrombin concentrated preparations are so highly priced that they are subject to some restrictions on their use to DIC patients in terms of benefit coverage by health insurance (e.g., such preparations are only permitted legislatively to be administered to patients with a blood antithrombin III level of 70% or below of the normal one and also at a reduced frequency of within 5 days per month). In addition, heparin prolongs the blood coagulation time and makes patients more susceptible to a bleeding tendency. As is described in the above, the heparin therapy is not only accompanied with the adverse effect of increased bleeding tendency but also incurs much more treatment expenses in association with the inherent use of antithrombin III. Because of this, there is also used low-molecular-weight heparin which exhibits enhanced specificity for the blood coagulation factor Xa. However, the drug, like thrombin, is accompanied with the adverse effect of increased bleeding tendency, depending upon the dose, and accordingly requires troublesome management of its blood levels. Moreover, low-molecular-weight heparin likewise exhibits weaker thrombin inhibitory activity than heparin, and consumes antithrombin III to thereby suppress hypercoagulation. As is evident from the above, therapy with use of either of heparin and low-molecular-weight heparin involves increased bleeding tendency and consumption of antithrombin III, though to a varying extent.

SUMMARY OF THE INVENTION

Under these circumstances, the present inventors conducted repeatedly intensive research in an attempt to explore a possible means of inhibiting function of the blood coagulation system and also suppressing both hypercoagulation and clot formation without bringing about the adverse effect of increased bleeding tendency, and as a result, discovered that a protein with a molecular weight of 54 to 57 kDa existing in human urine unexpectedly suppresses in DIC consumption of fibrinogen, prolongation of prothrombin time and rise in blood FDP levels. This fact indicates that the said protein possesses suppressory activity against hypercoagulation.

DETAILED DESCRIPTION OF THE PREFERRED EMBODIMENT

With reference to the said protein, the purification method, typical properties and physico-chemical properties were previously published in several literature references [The Journal of Biological Chemistry, 261, 12759–12766 (1986), Method in Enzymology, 222, 385–399 (1993)], and the protein has been classified into a family of serine protease inhibitors. This protein, whose presence was already detected in urine as well as in blood and seminal fluid, is in many instances called protein C inhibitor, and is therefore to be referred to briefly as protein C inhibitor below throughout this specification, as well.

The present invention has been completed on the basis of the above novel finding and relates to suppressory agents against hypercoagulation which comprise as an effective ingredient protein C inhibitor with a molecular weight of 54 to 57 kDa being capable of suppressing function of the blood coagulation system.

Protein C inhibitor which is used in the present invention is present in urine and blood, and may be purified and separated from urine or blood. Protein C inhibitor can be purified and separated by subjecting urine or blood to an appropriate treatment such as centrifugation, followed by combinations of affinity column chromatography on metal chelate Sepharose and concanavalin A Sepharose and on heparin Sepharose with gel filtration column chromatography (refer to Example 1).

By following such procedure, there may be obtained protein C inhibitor with varied degrees of purity, and in order to assure administration of the effective ingredient at a specifically determined dose, it is preferable to use protein C inhibitor with as high a degree of purity as possible.

Protein C inhibitor according to the present invention, after being administered intravenously, can suppress both hypercoagulation and induction of the secondary fibrinolysis, without accompaniment of increased bleeding tendency (refer to Examples 2 and 3).

In order to suppress hypercoagulation, the suppressory agents against hypercoagulation according to the present invention can be administered to human adults through intravenous drip at a daily dose of 100 to 200 mg as a purified product. Protein C inhibitor, which is normally present in blood in proportions of 3.3 to 6.8 $\mu$g/ml, is observed to be almost free from toxicities after intravenous administration.

The present invention will be furthermore illustrated below by way of examples, but is not understood to be limited by such examples.

BRIEF DESCRIPTION OF THE DRAWING

FIG. 1 illustrates the electrophoresis patterns of protein C inhibitor as purified in Example 1, where staining was effected with 0.25% Coomassie Brilliant Blue, and the lanes M and 1 and 2 represent individually the molecular weight marker (from the top to the bottom, 200, 97.4, 68, 43, 29, 18.4 and 14.3 kDa), elution fraction A from the heparin column and gel filtration fraction B.

EXAMPLES

Example 1

(Production of Purified Protein C Inhibitor)

Figure 2:
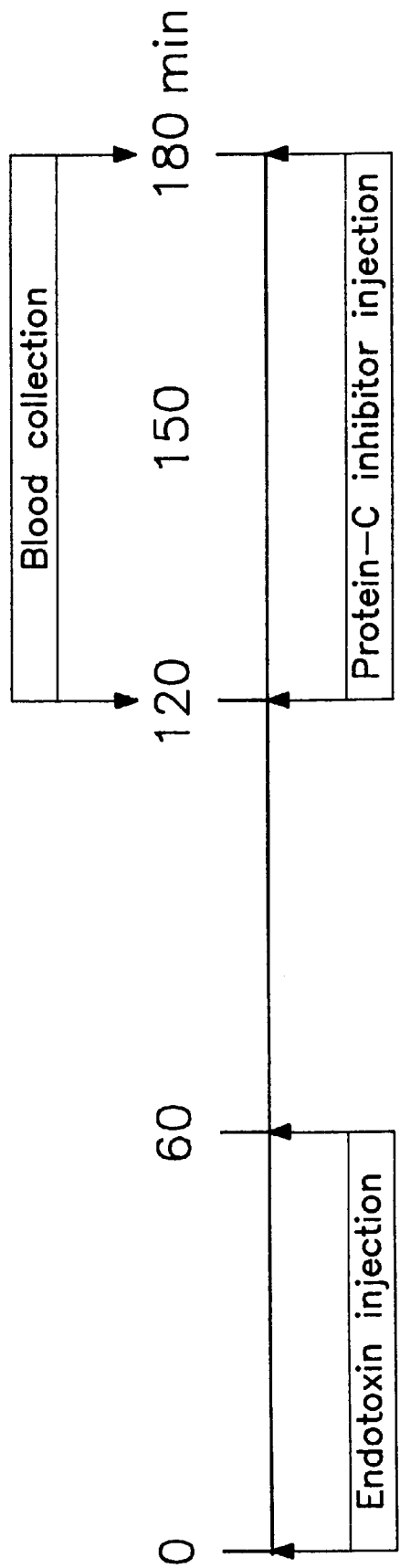
FIG. 2 is a time line, which charts the relative times of events as described in Example 3, herein.

All the steps of the below-described purification process were carried out at a temperature of 4° C. Human urine (30 liters) collected from healthy male adults in the presence of benzamidine (the final concentration of 5 mM) was frozen at −20° C., then thawed and centrifuged by a centrifuge (TOMY RS-20, manufactured by TOMY Co. of Tokyo, Japan) at 3,000 rpm for 30 min, and the resultant supernatant was adjusted to a pH value of 7.4 with sodium hydroxide (6N), followed by filtration through filter paper. The filtrate was applied to a column of zinc-chelate Sepharose (14×6.9 cm) equilibrated with 20 mM Tris-acetate buffer (pH 7.4) containing 300 mM of sodium chloride and 5 mM of benzamidine, and the column was washed with the same buffer, followed by elution with the same buffer supplemented with 50 mM of imidazole. The fractions showing the maximum absorption at a wavelength of 280 nm were collected and applied to a column of concanavalin A-Sepharose (2.5×7.1 cm) equilibrated with 20 mM Tris-acetate buffer (pH 7.4) containing 150 mM of sodium chloride, 5 mM of benzamidine and 1 mM of phenylmethylsulfonyl fluoride (hereinafter referred to briefly as "PMSF"), and after the buffer was replaced with 20 mm Tris-hydrochloride buffer (pH 7.4) containing 150 mM of sodium chloride, 5 mM of benzamidine and 1 mM of PMSF, the column was washed with 20 mM Tris-hydrochloride buffer (pH 7.4) containing 150 mM of sodium chloride, 1 mM of benzamidine and 1 mM of PMSF, followed by elution with the same buffer containing 500 mM of methyl-α-D-glycoside. Then, the fractions showing the maximum absorption at a wavelength of 280 nm were collected and electrophoresed against 20 mM Tris-hydrochloride buffer (pH 7.4) containing 50 mM of sodium chloride, 5 mM of benzamidine and 1 mM of PMSF until the inner solution showed the same electrical conductivity (4.5 mS/cm) as the said buffer did.

The electrophoresed inner solution was applied to a column of heparin-Sepharose (1.5×4.5 cm) equilibrated with 20 mM Tris-hydrochloride buffer (pH 7.4) containing 50 mM of sodium chloride, 5 mM of benzamidine and 1 mM of PMSF, and the column was washed with 20 mM Tris-hydrochloride buffer (pH 7.4) containing 200 mM sodium chloride, followed by elution with 20 mM Tris-hydrochloride buffer (pH 7.4) containing 500 mM of sodium chloride to collect the fractions (Fraction A) acting to prolonged the prothrombin time (to inhibit accelerated function of the blood coagulation system) of standard human blood plasma (supplied by George King Bio-Medical Co.). Said Fraction A was subjected to gel filtration through a column for gel filtration (TSK-G 3000XL) equilibrated with 20 mM Tris-hydrochloride buffer containing 300 mM of sodium chloride, and the fraction (Fraction B) showing a major peak was recovered by separation and stored as frozen at −20° C. until use.

The above-described purification process yielded about 600 $\mu$g of protein C inhibitor from 30 liters of human fresh urine, as quantitatively determined by use of a commercially available kit for quantitative determination of protein C inhibitor (PCI antigen ELISA kit, supplied by Technoclone Co.).

Figure 1:
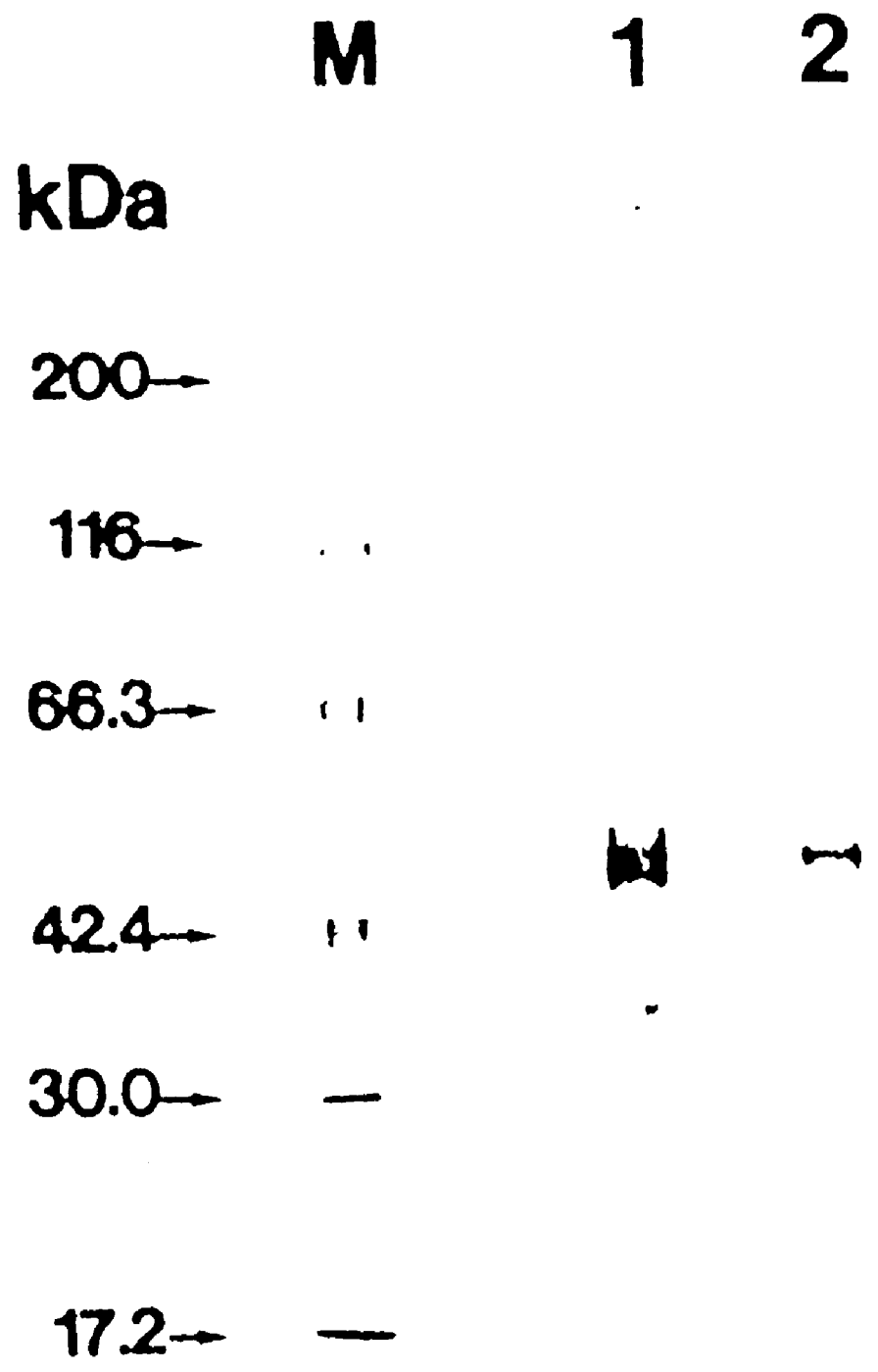

Fractions A and B as mentioned above were subjected to electrophoresis, with the electrophoresis patterns of protein C inhibitors being shown in FIG. 1, wherein staining was effected with 0.25% Coomassie Brilliant Blue, and the lanes M and 1 and 2 represent individually the molecular weight markers (from the top to the bottom, 200, 116, 66.3, 42.4, 30.0 and 17.2 kDa), elution fraction A from the heparin-column and gel filtration fraction B.

Example 2

(Preparation of Endotoxin-induced DIC Model Rat)

One of the reasons why DIC arises is bacterial infection. Endotoxin produced by bacteria triggers blood coagulation by causing tissue factor expression on the surface of endothelial cells. Accordingly, endotoxin was utilized to create a DIC model rat by the procedure described below in detail:

Each of three male rats (each weighing 170 to 200 g) under anesthesia with pentobarbital were injected with 50 mg/kg weight of endotoxin (E. coli 0127:D8, supplied by DIFCO CO.) through the tail vein at a constant speed over the 60-min period, followed by continued observation for 180 min. after initiation of the endotoxin injection; namely, blood was drawn in each 300 $\mu$l portion from the jugular vein at 5 different points of time of before initiation of the endotoxin injection as well as 90, 120, 150 and 180 min. after initiation of the endotoxin injection. The drawn blood samples were used in the below-described tests (a), (b) and (c). Immediately after the observations, moreover, 1800 $\mu$l of blood was drawn through inferior vena cava with use of a syringe containing 200 $\mu$l of 3.8% sodium citrate solution and centrifuged to give the blood plasma, which was used as a sample for the determination of the prothrombin time (d).

(a) Platelet count

In order to calculate the platelet count in blood, a 100 μl volume of the blood drawn at each point of time as mentioned above was placed in a blood collection bottle (supplied by Sysmex Co.) being provided with a coating of ethylenediamine-tetraacetic acid as an anticoagulant. Measurement of the blood samples with an automatic hemoanalyzer (supplied by Sysmex co.) revealed that the platelet count as determined at 90 min after initiation of the endotoxin injection hardly differed from the baseline before the endotoxin injection, whereas the platelet counts at 120 and 180 min. after initiation of the endotoxin injection decreased down to 75.0±4.1% and 50.2±1.5% of the baseline before initiation of the endotoxin injection, respectively.

(b) Fibrinogen level

A 90 μl volume each of the blood samples taken at the above pints of time was added to 10 μl of 9.8% sodium citrate, respectively, followed by centrifugation to give the blood plasma samples, which were subjected individually to a fibrinogen test kit (supplied by Wako Pure-Chemicals Ind. of Japan) to thereby determine their plasma fibrinogen levels. The test results indicated that the fibrinogen level at 90 min after initiation of the endotoxin injection did not differ from the baseline before initiation of the endotoxin injection, whereas the fibrinogen levels at 120 and 180 min. after initiation of the endotoxin injection dropped to 80.7±6.6% and 41.0±3.7% of the baseline before initiation of the endotoxin injection, respectively.

(c) FDP level

A 100 μl volume each of the blood samples taken at the above points of time was clotted with a coagulation promoter attached to a FDP test kit (supplied by Teikoku Zohki Co. of Japan), respectively, followed by centrifugation to give the serum samples, which were determined for individual FDP levels with use of the said test kit. The test results indicated that no FDP was detected at the point of time up to 90 min. after initiation of the endotoxin injection, whereas the FDP levels increased to 3.3±1.4 (μg/ml) and 20.0±0.0 (μg/ml) individually at 120 and 180 min after initiation of the endotoxin injection, suggesting accelerated function of the fibrinolytic system at 120 min after initiation of the endotoxin injection or thereafter.

(d) Prothrombin time

A 100 μl volume of the blood plasma sample as obtained by the above procedure was measured with a measurement kit for prothrombin time (supplied by Wako Pure-Chemicals Ind. of Japan), with the result that the prothrombin time was found to be 26.5±1.9 sec. and prolonged markedly as compared with the baseline time of 12.6±0.4 sec. before the endotoxin injection. This demonstrated that the extrinsic blood coagulation factors were consumed rapidly.

Tabulated below in Table 1 were the results of the tests (a), (b), (c) and (d).

TABLE 1

Effects of endotoxin on parameters of blood coagulation and fibrinolysis

| | | After initiation of the endotoxin injection | | |
|---|---|---|---|---|
| | Before | 90 | 120 | 180 min |
| Platelet count, % | 100 | 100 ± 5.0 | 75 ± 4.1 | 50.2 ± 1.5 |
| Fibrinogen level, % | 100 | 100 ± 2.5 | 80.7 ± 6.6 | 41.0 ± 3.7 |
| FDP (μg/ml) | N.D. | N.D. | 3.3 ± 1.4 | 20.0 ± 0.0 |
| Prothrombin time, sec. | 12.6 ± 0.4 | — | — | 26.5 ± 1.9 |

Notes:
Each figure designates mean ± standard deviation.

"FDP" and "N.D." stand for "fibrin/fibrinogen degradation products" and "not detected", respectively.

As is evident from the above, the results of the tests (a) and (b) indicate that marked clot formation took place from hypercoagulation as from 120 min. after initiation of the endotoxin injection onward, and those of the test (c) reveal the induction of fibrinolysis accompanied by hypercoagulation, while those of the test (d) show that in the DIC model, there arose abrupt consumption of the coagulation factors; namely, it was found out that the present DIC model suffers from typical hypercoagulation as is often noticed in DIC as from 120 min. after initiation of the endotoxin injection.

In view of the above, the rats having 120 min. elapsed after initiation of the endotoxin injection were utilized as an endotoxin-induced DIC model in Example 3.

Example 3

(Effects of Protein C Inhibitor on the Endotoxin-induced DIC Model Rat)

A 1-ml volume each of Protein C inhibitor (90 μg/ml) obtained in Example 1 and 20 mM Tris-hydrochloride buffer (pH 7.4) containing 300 mM sodium chloride were injected. individually to the endotoxin-induced DIC model rats (divided into groups each consisting of 3 heads) having 120 min. elapsed after initiation of the endotoxin injection through the femoral vein at a constant rate over the 60-min. period, and the blood samples, which were drawn at the different points of time indicated in FIG. 2, or before initiation of the injection of protein C inhibitor or the buffer (120 min.) and 30 min (150 min.) and 60 min. (180 min.) after initiation of the injection, were determined for platelet count, fibrinogen level and FDP level. Immediately after conclusion of the observation (180 min), additionally, a 180 μl volume of blood was collected from each rat through inferior vena cava with use of a syringe containing 200 μl of 3.8% sodium citrate, followed by centrifugation, and the resultant blood plasma was subjected to measurement of the prothrombin time.

Table 2 and FIG. 2 illustrate these test procedural steps and the test results.

TABLE 2

Effects of endotoxin on the parameters of blood coagulation and fibrinolysis in the DIC model

|  | Control Group | | | Treated Group | | |
|---|---|---|---|---|---|---|
|  | After initiation of the injection | | | | | |
|  | Buffer | | | Protein C inhibitor | | |
|  | Before | 30 | 60 | Before | 30 | 60 |
| Platelet count, % | 100 | 75.2 ± 9.9 | 67.1 ± 1.8 | 100 | 78.9 ± 6.3 | 68.2 ± 7.6 |
| Fibrinogen level, % | 100 | 75.2 ± 3.3 | 50.8 ± 2.8 | 100 | 93.4 ± 7.9* | 64.7 ± 2.0* |
| FDP (μg/ml) | 3.3 ± 1.4 | 11.7 ± 7.6 | 20.0 ± 0.0 | 2.5 ± 0.0 | 5.0 ± 0.0 | 10.0 ± 0.0* |
| Prothrombin time, sec. | — | — | 26.5 ± 1.9 | — | — | 20.4 ± 0.5* |

Notes:
(1) Each figure is expressed in mean ± standard deviation, * $P < 0.05$, as compared with the group treated through the buffer injection at each point of time (Dunnett's test for platelet count and fibrogen, and Scheffé's test for FDP and prothrombin time).
(2) "FDP" stands for "fibrin/fibrinogen degradation products".

At each point of time of collecting blood samples (namely, before initiation of the injection of protein C inhibitor or buffer, and 30 and 60 min after initiation of the injection), the platelet count and fibrinogen and FDP levels in blood were measured and determined. Comparison between the two treated groups for decreases (%) in platelet count indicated that there was no difference noted at 30 and 60 min. after initiation of the injection. Also comparative investigation was conducted into fibrinogen levels in blood plasma which represented the degree of utilization and consumption for the formation of thrombi or clots, leading to the conclusion that the control group at 30 and 60 min. showed the decrease levels of 75.2±3.3 and 50.8±2.8 (%) from the baseline before initiation of the injection, respectively, whereas the group treated through administration of protein C inhibitor exhibited significantly suppressed decreases as reflected by the individual determined levels of 93.4±7.9 and 64.7±2.0 (%). In view of the fact that the model animals were generated through function of the extrinsic blood coagulation system, consumption of the extrinsic coagulation factors was studied by measuring the prothrombin time in blood plasma (12.6±0.4 sec. measured for the blood plasma from normal rats) immediately after conclusion of the observation (180 min), resulting in the finding that the control group showed the prothrombin time of 26.5±1.9 sec., whereas the group treated through administration of protein C inhibitor significantly shortened prothrombin time of 12.6±0.4 sec., approaching the normal value. On the other hand, comparative investigation was carried out into blood FDP levels which are considered as an index for the induction of fibrinolysis brought about through function of the blood coagulation system, revealing that the control group showed increased levels as high as 11.7±7.6 and 20.0±0.0 (μg/ml) at 30 and 60 min. after initiation of the injection, respectively, whereas the group treated through administration of protein C inhibitor exhibited suppressed increases in FDP level to as low as 5.0±0.0 and 10.0±0.0 (μg/ml).

The above results demonstrated that in such diseases as DIC which involve hypercoagulation, protein C inhibitor can suppress a decrease (consumption) of fibrinogen, a factor involved in thrombopoiesis, and consumption of the extrinsic coagulation factors, without suppressing platelet aggregation which is important for formation of hemostatic thrombi (white thrombi). Furthermore, it was found that protein C inhibitor, with its suppressory activity against hypercoagulation, can also suppress the induction of secondary fibrinolysis.

Consequently, it can be said that protein C inhibitor possesses suppressory activity against repetition of blood coagulation and thrombolysis taking place frequently in DIC without accompaniment of adverse effects such as bleeding tendency.

We claim:

1. A method for treating hypercoagulation in a mammal in need of such treatment comprising administering to the mammal an effective amount of protein C inhibitor.

2. The method of claim 1, wherein the administering is by intravenous injection.

3. The method of claim 1, wherein the protein C inhibitor is a protein C inhibitor fraction obtained through purification and separation from human urine or blood.

* * * * *

UNITED STATES PATENT AND TRADEMARK OFFICE
CERTIFICATE OF CORRECTION

PATENT NO. : 5,948,752  Page 1 of 1
DATED : September 7, 1999
INVENTOR(S) : Mitsugu Fujita et al.

It is certified that error appears in the above-identified patent and that said Letters Patent is hereby corrected as shown below:

<u>Title page,</u>
In the illustrative figure and Fig. 2, the hyphen "-" in "Protein-C" should be deleted.

<u>Column 3,</u>
Lines 25-26, change series of figures "200, 97.4, 68, 43, 29, 18.4 and 14.3" to
-- 200, 116, 66.3, 42.4, 30.0 and 17.2 --

<u>Columns 7 and 8,</u>
TABLE 2, change the title "Effects of endotoxin in the parameters of blood coagulation and fibrinolysis in the DIC model" to -- Protein C inhibitor as given the DIC model rats i.v. in relation to changes in the parameters of blood coagulation and fibrinolysis --

<u>Column 7,</u>
Line 48, change "12.6±0.4" to -- 20.4±0.5 --

Signed and Sealed this

Fourth Day of February, 2003

JAMES E. ROGAN
*Director of the United States Patent and Trademark Office*